US011597912B2

(12) United States Patent
Kim et al.

(10) Patent No.: US 11,597,912 B2
(45) Date of Patent: Mar. 7, 2023

(54) METHOD OF PRODUCING REGULATORY T CELLS BY CULTURING REGULATORY T CELLS OBTAINED FROM UMBILICAL CORD BLOOD

(71) Applicant: TERAIMMUNE, INC., Gaithersburg, MD (US)

(72) Inventors: Yong Chan Kim, Gaithersburg, MD (US); Nari Byun, Gaithersburg, MD (US); Jeong Heon Yoon, Gaithersburg, MD (US)

(73) Assignee: TERAIMMUNE, INC., Gaithersburg, MD (US)

( * ) Notice: Subject to any disclaimer, the term of this patent is extended or adjusted under 35 U.S.C. 154(b) by 0 days.

(21) Appl. No.: 17/709,979

(22) Filed: Mar. 31, 2022

(65) Prior Publication Data
US 2022/0325243 A1 Oct. 13, 2022

Related U.S. Application Data

(60) Provisional application No. 63/170,214, filed on Apr. 2, 2021.

(51) Int. Cl.
*C12N 5/0783* (2010.01)
*A61P 37/06* (2006.01)
*A61K 35/17* (2015.01)

(52) U.S. Cl.
CPC ............ *C12N 5/0637* (2013.01); *A61K 35/17* (2013.01); *A61P 37/06* (2018.01); *C12N 2500/40* (2013.01); *C12N 2501/04* (2013.01); *C12N 2501/15* (2013.01); *C12N 2501/2302* (2013.01)

(58) Field of Classification Search
None
See application file for complete search history.

(56) References Cited

U.S. PATENT DOCUMENTS

| 9,481,866 | B2 | 11/2016 | Kim et al. |
| 2005/0147983 | A1 | 7/2005 | Wilting et al. |
| 2012/0282694 | A1 | 11/2012 | Godfrey et al. |
| 2016/0194605 | A1 | 7/2016 | Scott et al. |
| 2017/0022478 | A1 | 1/2017 | Kim et al. |

OTHER PUBLICATIONS

International Search Report dated Sep. 1, 2022 in International Application No. PCT/US2022/022823.
Written Opinion of the International Searching Authority dated Sep. 1, 2022 in International Application No. PCT/US2022/022823.
GenBank Submission CP035492.1, "Paenibacillus protaetiae strain FW100M-2 chromosome, complete genome", Feb. 3, 2019 (3 pages total).
Erica G. Schmitt et al., "Generation and function of induced regulatory T cells", Frontiers in Immunology, Jun. 19, 2013, pp. 1-13, vol. 4, Article 152.
Sharvan Sehrawat et al., "Tregs and infections: on the potential value of modifying their function", Journal of Leukocyte Biology, Dec. 2011, pp. 1079-1087, 90(6).
Maria-Grazia Roncarolo et al., "Regulatory T-cell immunotherapy for tolerance to self antigens and alloantigens in humans", Nature Reviews, Immunology, Aug. 2007, pp. 585-598, vol. 7(8).
James L. Riley et al., "Human T Regulatory Cells as Therapeutic Agents: Take a Billion or So of These and Call Me in the Morning", Immunity, May 2009; pp. 656-665, 30(5).
Petra Hoffmann et al., "Donor-type CD4+CD25+ Regulatory T Cells Suppress Lethal Acute Graft-Versus-Host Disease after Allogeneic Bone Marrow Transplantation", J. Exp. Med., Aug. 5, 2002, pp. 389-399, vol. 196, No. 3.
Weihong Liu et al., "CD127 expression inversely correlates with FoxP3 and suppressive function of human CD4+ T reg cells", The Journal of Experimental Medicine, Jul. 10, 2006; pp. 1701-1711, vol. 203, No. 7.
K.L. Hippen et al., "Generation and large-scale expansion of human inducible regulatory T cells that suppress graft-versus-host disease", American Journal of Transplantation, Jun. 2011, pp. 1148-1157, 11(6).
Petra Hoffmann et al., "Only the CD45RA+subpopulation of CD4+ CD25high T cells gives rise to homogeneous regulatory T-cell lines upon in vitro expansion", Blood, Dec. 15, 2006, pp. 4260-4267, vol. 108, No. 13.

*Primary Examiner* — Amy E Juedes
(74) *Attorney, Agent, or Firm* — Sughrue Mion, PLLC

(57) ABSTRACT

The present disclosure provides a method for producing a population of regulatory T cells comprising culturing an initial population of regulatory T cells obtained from umbilical cord blood in a media comprising an oligonucleotide having the sequence of AATCGTAACCGTCGTATCGGC-GAT (SEQ ID NO: 1) to expand the initial population of regulatory T cells, and a method of treating an autoimmune disease comprising administering to a subject in need thereof an effective amount of a composition comprising the regulatory T cells prepared by the above method.

5 Claims, 8 Drawing Sheets

Specification includes a Sequence Listing.

METHOD OF PRODUCING REGULATORY T CELLS BY CULTURING REGULATORY T CELLS OBTAINED FROM UMBILICAL CORD BLOOD

FIELD

Described herein are a method for producing regulatory T cells by culturing regulatory T cells obtained from umbilical cord blood, and a method of treating an autoimmune disease by administering a composition comprising the regulatory T cells to a subject in need thereof.

BACKGROUND

Regulatory T cells (Tregs) compose a small portion of the immune cell population and they can be divided into two subpopulations. One is generated and educated in the thymus and termed natural Tregs (nTregs). The other is generated in peripheral sites and termed induced Tregs (iTregs) (Schmitt E G and Williams C B Front. Immunol. 2013; 4(152):1-13). They are dedicated to deactivating excessive immune response and maintaining immune homeostasis (Sharvan Sehrawat, Barry T. Rouse J Leukoc Biol. 2011; 90(6): 1079-1087). Patients who suffer from Graft versus Host Disease (GVHD) or autoimmune diseases are known to have fewer Tregs than healthy donor or their function is abnormal (Roncarolo M G, Battaglia M., Nat Rev Immuno., 2007; 7(8):585-598; Riley J L, June C H, Blazar B R, Immunity, 2009; 30(5):656-665). With this reason, Treg transfusion can be a potential therapy to them. The preventive/therapeutic effect of Treg adoptive transfer was proved in mouse experiments (Hoffmann P, Ermann J, Edinger M, Fathman C G, Strober S, J Exp Med, 2002; 196(3):389-399). To apply the Tregs for a cell therapy or a clinical trial for the same, it requires large numbers and stable function of Tregs derived from peripheral blood or umbilical cord blood (UCB).

In an aspect of personalized cell therapy using a Treg, there are two major hurdles to overcome. First, the recipient needs a large number of cells of highly purified expanded Tregs. Second, Foxp3, which is the most important characteristic of Treg for its function, is easy to be lost in human Tregs during the expansion process. Many approaches have been used to address these problems. For instance, the combined use of $CD127^{lo}$ and $CD25^{high}$ was found to help isolating enriched populations of Foxp3+ T cells without contamination of $CD25^{int}$ T cells (Liu W, Putnam A L, Xu-Yu Z, et al., J Exp Med. 2006; 203(7):1701-1711). In addition, adding the mTOR inhibitors, such as rapamycin, was found to inhibit contamination of conventional T cells during expansion and enable the expansion of Tregs with high purity. (Hippen K L, Merkel S C, Schirm D K, et al., American Journal of Transplantation, 2011; 11(6): 1148-1157).

As compared to expanded peripheral blood-derived Tregs, umbilical cord blood-derived expanded Tregs showed a more naïve phenotype by expressing a high level of CD45RA, a marker of naïve T cells. Naïve Treg produced a low level of a pro-inflammatory cytokine such as IFN-γ after activation. Moreover, naïve Tregs maintain long-term phenotypic stability as compared to memory Tregs and it was proved by animal models and in vitro studies with the human specimens (Hoffmann, P, Eder, R, Boeld, T J, Doser, K, Piseshka, B, Andreesen, R, et al. Blood 2006; 108: 4260-4267).

Therefore, there has been a need for an efficient method of isolating and expanding stable regulatory T cells from human cord blood (umbilical cord blood).

SUMMARY

The present disclosure provides a method for producing a population of regulatory T cells comprising culturing an initial population of regulatory T cells obtained from umbilical cord blood in a media comprising an oligonucleotide having the sequence of AATCGTAACCGTCGTATCGGCGAT (SEQ ID NO: 1) to expand the initial population of regulatory T cells.

In an exemplary embodiment, the media may further comprise TGFβ1. In addition, in an exemplary embodiment, the media may further comprise rapamycin. In another exemplary embodiment, the media may further comprise both of TGFβ1 and rapamycin such that an initial population of regulatory T cells obtained from umbilical cord blood is cultured in the presence of the oligonucleotide of SEQ ID NO: 1, TGFβ1 and rapamycin.

In one embodiment, the initial population of regulatory T cells may be enriched for $CD4^+CD25^{+/hi}CD127^{lo/-}$ FoxP3$^+$.

The present disclosure also provides a population of regulatory T cells prepared by culturing an initial population of regulatory T cells obtained from umbilical cord blood in a media comprising an oligonucleotide of SEQ ID NO: 1 to expand the initial population of regulatory T cells.

In addition, the present disclosure provides a method of treating an autoimmune disease comprising administering to a subject in need thereof an effective amount of a composition comprising regulatory T cells prepared by culturing an initial population of regulatory T cells obtained from umbilical cord blood in a media comprising an oligonucleotide of SEQ ID NO: 1 to expand the initial population of regulatory T cells.

In one embodiment, the autoimmune disease is selected from the group consisting of type I diabetes, multiple sclerosis, Graft versus host disease, allograft rejection, atopic dermatitis, psoriasis, inflammatory bowel disease, neuromyelitis optica, rheumatoid arthritis, alopecia areata, systemic lupus erythematosus, pemphigus vulgaris, autoimmune vasculitis, xenogeneic organ transplantation, allogenic organ transplantation, and anti-drug antibody-mediated complications.

BRIEF DESCRIPTION OF THE DRAWINGS

FIG. 1 shows that on day 0, sorted CD4$^+$ enriched T cells were seeded and activated with TransAct in T cell culture media containing TGFβ1 (2 ng/mL) and BHKps25 (2 μM; oligonucleotide of SEQ ID NO: 1) until day 5. The rapamycin (100 nM) was supplied to remove the contaminated conventional T cell population from day 3 to 5. Expanded Tregs were re-stimulated by adding autologous feeder cells with anti-CD3 (clone OKT3) antibody on day 6. Phenotype analysis was conducted on days 10 and 17. The BHKps25 (oligonucleotide of SEQ ID NO: 1) was removed from T cell media from day 13 to the end of the expansion.

In FIG. 2, umbilical cord blood (UCB) was enriched by human CD4 MicroBeads and sorted on a Melody cell sorter using Chorus software. The singlet was gated on the lymphocyte gate (data not shown). Next, CD4$^+$ population was gated followed by gating the naïve T cells (CD4$^+$CD25$^{-/lo}$CD127$^+$CD45RA$^+$) and Treg (CD4$^+$CD25$^{hi}$CD127$^{lo}$). Both sorted Treg and naïve T cell populations showed high purity above 97%. Naïve T cells were used as a control.

In FIG. 3, mononuclear cells from UCB (A-B) and PBMC (C-D) were analyzed on day 0. The expression levels of Foxp3 and Helios were measured from UCB (A) or PBMC (C) derived mononuclear cells in live $CD4^+$ populations. The percentage of naïve T cells was measured from UCB (B) or PBMC (D) derived $CD25^{hi}CD127^{lo}$ and $CD25^{-/lo} CD127^+$ cells in live $CD4^+$ population.

DETAILED DESCRIPTION

Figure 1:
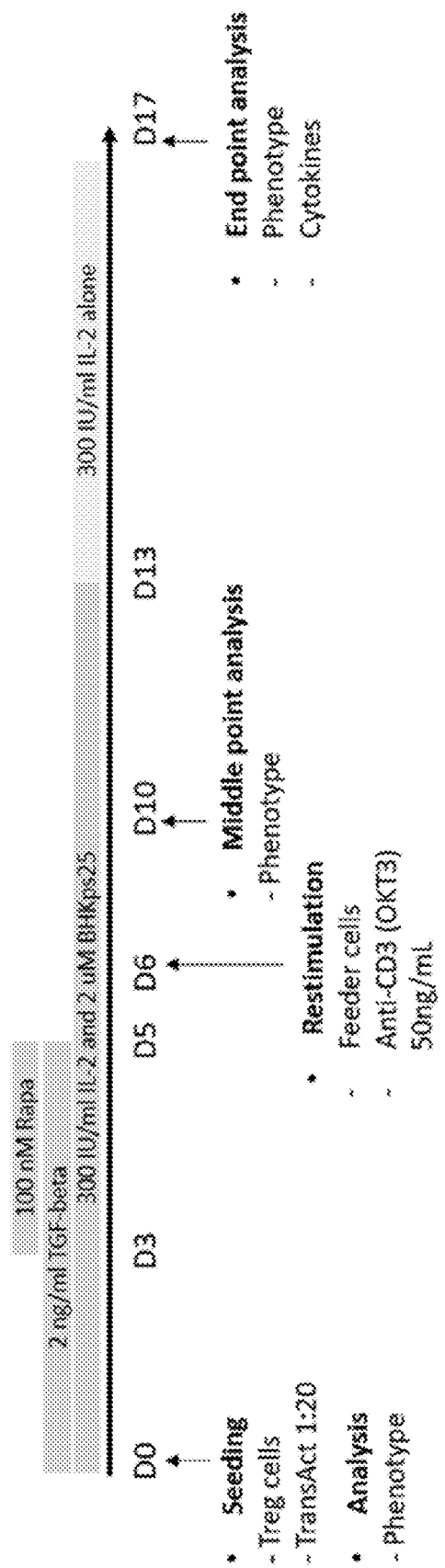
FIG. 1 shows a scheme of the Treg expansion. In particular.

The present disclosure relates to a method for producing a population of regulatory T cells comprising culturing an initial population of regulatory T cells obtained from umbilical cord blood in a media comprising an oligonucleotide having the sequence of AATCGTAACCGTCGTATCGGCGAT (SEQ ID NO: 1) to expand the initial population of regulatory T cells.

The term umbilical cord blood, also called cord blood, refers to blood that remains in the placenta and in the attached umbilical cord after childbirth.

The term regulatory T cells refer to a subpopulation of T cells that modulate the immune system, maintain tolerance to self-antigens, and prevent autoimmune disease.

The term oligonucleotide refers to a polymer of nucleotides (or bases) which can be synthesized or generated by degradation of a larger nucleic acid molecule. In an exemplary embodiment, the oligonucleotide is a phosphorothioate-backboned oligodeoxynucleotide. The oligonucleotide of SEQ ID NO: 1 may be added to a media in an amount of 0.01 to 20 µM. In another embodiment, the lower limit of the amount of the oligonucleotide of SEQ ID NO: 1 may be 0.2, 0.3, 0.4, 05, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4 or 2.5 µM. The upper limit of the amount of the oligonucleotide of SEQ ID NO: 1 may be 15, 10, 9, 8, 7, 6, 5, 4.5, 4.0, 3.5, 3.0, 2.9, 2.8, 2.7, 2.6, 2.5, 2.4, 2.3, 2.2, 2.1 or 2.0 µM. The upper limit and lower limit of the amount of the oligonucleotide of SEQ ID NO: 1 may be combined to provide a different amount range. In addition, the amount of the oligonucleotide of SEQ ID NO: 1 may be in any amount within such combinations. For instance, the amount of the oligonucleotide of SEQ ID NO: 1 may be 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 µM. In another embodiment, analogs of the oligonucleotide of SEQ ID NO: 1 may be used instead of or together with the oligonucleotide of SEQ ID NO: 1.

In one embodiment, instead of the oligonucleotide of SEQ ID NO: 1, other oligonucleotides may be used in culturing an initial population of regulatory T cells obtained from umbilical cord blood if they perform substantially the same function as the oligonucleotide of SEQ ID NO: 1. Such oligonucleotides may be 300 nucleotides or less in length, 200 nucleotides or less in length, 100 nucleotides or less in length, 90 nucleotides or less in length, 80 nucleotides or less in length, 70 nucleotides or less in length, 60 nucleotides or less in length, 50 nucleotides or less in length, 40 nucleotides or less in length, 30 nucleotides or less in length, 29 nucleotides or less in length, 28 nucleotides or less in length, 27 nucleotides or less in length, 26 nucleotides or less in length, 25 nucleotides or less in length, 24 nucleotides or less in length, 23 nucleotides or less in length, 22 nucleotides or less in length, 21 nucleotides or less in length, 20 nucleotides or less in length, 19 nucleotides or less in length, 18 nucleotides or less in length, 17 nucleotides or less in length, 16 nucleotides or less in length, 15 nucleotides or less in length, 14 nucleotides or less in length, 13 nucleotides or less in length, 12 nucleotides or less in length, 11 nucleotides or less in length, 10 nucleotides or less in length, 9 nucleotides or less in length, 8 nucleotides or less in length, or 7 nucleotides or less in length.

In addition, such oligonucleotides may be 7 nucleotides or greater in length, 8 nucleotides or greater in length, 9 nucleotides or greater in length, 10 nucleotides or greater in length, 11 nucleotides or greater in length, 12 nucleotides or greater in length, 13 nucleotides or greater in length, 14 nucleotides or greater in length, 15 nucleotides or greater in length, 16 nucleotides or greater in length, 17 nucleotides or greater in length, 18 nucleotides or greater in length, 19 nucleotides or greater in length, 20 nucleotides or greater in length, 20 nucleotides or greater in length, 21 nucleotides or greater in length, 22 nucleotides or greater in length, 23 nucleotides or greater in length, 24 nucleotides or greater in length, 25 nucleotides or greater in length, 26 nucleotides or greater in length, 27 nucleotides or greater in length, 28 nucleotides or greater in length, 29 nucleotides or greater in length, 30 nucleotides or greater in length, 40 nucleotides or greater in length, 50 nucleotides or greater in length, 60 nucleotides or greater in length, 70 nucleotides or greater in length, 80 nucleotides or greater in length, 90 nucleotides or greater in length, 100 nucleotides or greater in length, or 200 nucleotides or greater in length.

The upper limit and lower limit of the nucleotide length range above may be combined to provide a different nucleotide length range. For instance, oligonucleotides may be 20 nucleotides or greater and 30 nucleotides or less in length where 30 nucleotides or greater in length and 20 nucleotides or greater are combined to provide a nucleotide length range. In addition, oligonucleotides may be in any nucleotide length within such combinations. For instance, oligonucleotides may be 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, 29 nucleotides in length, or 30 nucleotides in length.

In an exemplary embodiment, the media may further comprise TGFβ1. The TGFβ1 (Transforming growth factor beta 1) is a polypeptide member of the transforming growth factor beta superfamily of cytokines. In an exemplary embodiment, TGFβ1 may be added to a media in an amount of 0.1 to 10 ng/mL. In another embodiment, the lower limit of the amount of TGFβ1 may be 0.2, 0.3, 0.4, 05, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4 or 2.5 ng/mL, and the upper limit of the amount of TGFβ1 may be 9, 8, 7, 6, 5, 4.5, 4.0, 3.5, 3.0, 2.9, 2.8, 2.7, 2.6, 2.5, 2.4, 2.3, 2.2, 2.1 or 2.0 ng/mL. The upper limit and lower limit of the amount of TGFβ1 above may be combined to provide a different amount range. In addition, the amount of TGFβ1 may be in any amount within such combinations. For instance, the amount of TGFβ1 may be 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 ng/mL. In another embodiment, analogs of TGFβ1 may be used instead of or together with TGFβ1.

In addition, in an exemplary embodiment, the media may further comprise rapamycin. The rapamycin, also called sirolimus, is a mTOR inhibitor. In another embodiment, analogs of rapamycin may be used instead of or together with rapamycin. The rapamycin may be added to a media in an amount of 0.1 to 1000 nM. In another embodiment, the lower limit of the amount of rapamycin may be 1, 10, 20, 30, 40, 50, 55, 60, 65, 70, 75, 80, 85, 90, 95, 96, 97, 98 or 99 nM, and the upper limit of the amount of rapamycin may be 900, 800, 700, 600, 500, 400, 300, 200, 190, 180, 170, 160, 150, 145, 140, 135, 130, 125, 120, 115, 110, 109, 108, 107, 106, 105, 104, 103, 102 or 101 nM. The upper limit and lower limit of the amount of rapamycin above may be combined to provide a different amount range. In addition, the amount of rapamycin may be in any amount within such combinations. For instance, the amount of rapamycin may be 50, 60, 70, 80, 90, 95, 96, 97, 98, 99, 100, 101, 102, 103, 104, 105, 110, or 120 mM. In another embodiment, analogs of rapamycin may be used instead of or together with rapamycin.

In another exemplary embodiment, the media may further comprise both of TGFβ1 and rapamycin such that an initial population of regulatory T cells obtained from umbilical cord blood is cultured in the presence of the oligonucleotide of SEQ ID NO: 1, TGFβ1 and rapamycin. The amount for each of the oligonucleotide of SEQ ID NO: 1, TGFβ1 and rapamycin may be selected in any amount or ranges discussed above. In addition, analogs of the oligonucleotide of SEQ ID NO: 1, TGFβ1 and/or rapamycin may be used instead of or together with the oligonucleotide of SEQ ID NO: 1, TGFβ1 and rapamycin. In one embodiment, the oligonucleotide of SEQ ID NO: 1, TGFβ1 and rapamycin may be added to a medium in a different period. For instance, the oligonucleotide of SEQ ID NO: 1 may be added to a media in a period of day 0 to day 13 of culturing. The TGFβ1 may be added to a media in a period of day 0 to day 5 of culturing. The rapamycin may be added to a media in a period of day 3 to day 5 of culturing.

In one embodiment, the present disclosure provides a method of isolating and expanding nTreg from umbilical cord blood, comprising treating sorted CD4$^+$CD25$^{hi}$CD127$^{lo}$ Tregs from umbilical cord blood derived CD4 enriched T cells using CD4 microbeads with BHKps25 (the oligonucleotide of SEQ ID NO. 1), TGFβ1, and rapamycin in AIM-V media including human serum AB and IL-2.

In one embodiment, the present disclosure provides a method of keeping Foxp3 and Helios levels high in umbilical cord blood derived nTreg. In another embodiment, the present disclosure relates to a method of decreasing, inhibiting and/or lowering the secretion of proinflammatory cytokines such as IL-2, IL-4, IL-17A, and IFNγ in umbilical cord blood derived nTreg.

In one embodiment, the initial population of regulatory T cells may be enriched for CD4$^+$CD25$^{+/hi}$CD127$^{lo/-}$ FoxP3$^+$. Enrichment can be accomplished by any suitable separation method including, but not limited to, the use of a separation medium, cell size, shape or density separation by filtration or elutriation, immunomagnetic separation, fluorescent separation (e.g., fluorescence activated cell sorting system, FACS), or bead based column separation.

The present disclosure also provides a population of regulatory T cells prepared by culturing an initial population of regulatory T cells obtained from umbilical cord blood in a media comprising an oligonucleotide of SEQ ID NO: 1 to expand the initial population of regulatory T cells.

In addition, the present disclosure provides a method of treating an autoimmune disease comprising administering to a subject in need thereof an effective amount (e.g., therapeutically effective amount of therapeutically effective dosage) of a composition comprising regulatory T cells prepared by culturing an initial population of regulatory T cells obtained from umbilical cord blood in a media comprising an oligonucleotide of SEQ ID NO: 1 to expand the initial population of regulatory T cells.

The term administering refers to the physical introduction of an agent (composition) to a subject, using any of the various methods and delivery systems known to those skilled in the art. Exemplary routes of administration for the regulatory T cells prepared by the methods disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the regulatory T cells prepared by the methods disclosed herein is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "therapeutically effective amount" or "therapeutically effective dosage," as used herein, refers to an amount of the regulatory T cells that are produced by the methods and that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of the regulatory T cells to promote disease regression can be evaluated using a variety of methods known to the skilled practitioner, such as in human subjects during clinical trials, in animal model systems predictive of efficacy in humans, or by assaying the activity of the agent in in vitro assays.

The term treatment or treating of a subject refers to any type of intervention or process performed on, or the administration of one or more regulatory T cells prepared by the method disclosed herein to the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

In one embodiment, the autoimmune disease is selected from the group consisting of type I diabetes, multiple sclerosis, Graft versus host disease, allograft rejection, atopic dermatitis, psoriasis, inflammatory bowel disease, neuromyelitis optica, rheumatoid arthritis, alopecia areata, systemic lupus erythematosus, pemphigus vulgaris, autoimmune vasculitis, xenogeneic organ transplantation, allogenic organ transplantation, and anti-drug antibody-mediated complications.

Examples

Materials and Methods

Recombinant human interleukin (IL)-2 (GMP grade) was purchased from the R&D system. BHKps25 (Phosphorothioate-backboned oligodeoxynucleotides; SEQ ID NO: 1) was synthesized by TriLink biotechnologies. MACS GMP T cell TransAct was purchased from Miltenyi Biotec. Recombinant human TGFβ1 (preclinical grade) was purchased from Cell Genix Inc. Rapamycin was purchased from Sigma-Aldrich. Complete media for Treg culture (TCM) is AIM-V medium with 5% human AB serum, 500 units/mL penicillin, 500 mg/mL streptomycin, 1.46 mg/mL Glutamine containing 300 IU/mL of IL-2. During the culture, 100 nM of rapamycin and 2 ng/mL of hTGFβ1 were added according to the culture schedule.

Enrichment, Sorting, and Expansion of Regulatory T Cells from UCB

Umbilical cord blood (UCB) was purchased from Stem cell express. Cells were enriched with human CD4 Micro-Beads (Miltenyi Biotec Inc.) according to the manufacturer's instructions. Enriched cells were stained and then sorted into two populations. For staining, anti-human CD4-FITC, anti-human CD25-PE-Cy7, anti-human CD127-APC, and anti-human CD45RA-APC-Cy7 were purchased from Tonbo and Biolegend. Both Treg (CD4$^+$CD25$^{hi}$CD127$^{lo}$) and naïve T cells (CD4$^+$CD25$^{-/lo}$ CD127$^+$CD45RA$^+$) were sorted by Melody cell sorter (BD Bioscience).

To culture sort-isolated cells, TransAct was added into culture media directly on day 0 (FIG. 1) and cells were cultured in TCM in the presence of BHKps25 (2 μM; SEQ ID NO: 1) for 2 weeks. TGFβ1 (2 ng/mL) and rapamycin were provided in a different period as shown in FIG. 1, respectively. After 2 weeks of culture, cells were maintained in BHKps25 (SEQ ID NO: 1) free media until they were frozen.

For the 2$^{nd}$ stimulation of cultured Tregs, autologous feeder cells which were mitomycin C-treated CD4$^-$ cell was provided at 1:10 ratio with 50 ng/mL of anti-CD3 antibody (clone OKT3). If cells grow well on days 6-8 still, the 2$^{nd}$ stimulation is not required.

Intracellular Staining for Foxp3, Helios, and Cytokines

The phenotype and cytokine expression level of expanded Tregs were analyzed by flow cytometry at the endpoint of cultures as shown in the scheme (FIG. 1). Anti-human antibodies for CD3-BV570, CD4-FITC, CD8-BV421, CD25-BV785, CD127-APC, CD45RA-APC-Cy7, and live/dead cell stain kit were used for surface staining. They were purchased from Tonbo, Biolegend, and Invitrogen. Stained cells were fixed and permeabilized with Foxp3/Transcription factor fixation/permeabilization kit according to the manufacturer's instruction. After this step, intracellular staining was conducted with anti-Foxp3-PE-Cy7 and anti-Helios-PE antibodies. The phenotype of Treg was confirmed on days 0, 10, and 17. For cytokine analysis, expanding Tregs were cultured in IL-2 free media for 24 hours and naïve T cells were rested in IL-2 free media for 48 hours. Restimulation of day 17 was done by PMA and Ionomycin cocktail in the presence of brefeldin A for 4 hours at 37° C. Cells were fixed with a 2% paraformaldehyde solution. These cells were permeabilized with PBS containing bovine serum albumin and 0.1% Triton X-100. Antibodies for human CD4-FITC, Foxp3-PE-Cy7, Helios-PE, IL-2-BV510, IFN-γ-PerCP-Cy5.5, IL-4-BV421, and IL-17A-AF647 were stained at the same time. Stained cells were acquired on NovoCyte 3000 (Agilent) and analyzed using Flowjo software.

Results

Gating Strategy and Isolation of Tregs from Umbilical Cord Blood

Figure 2:
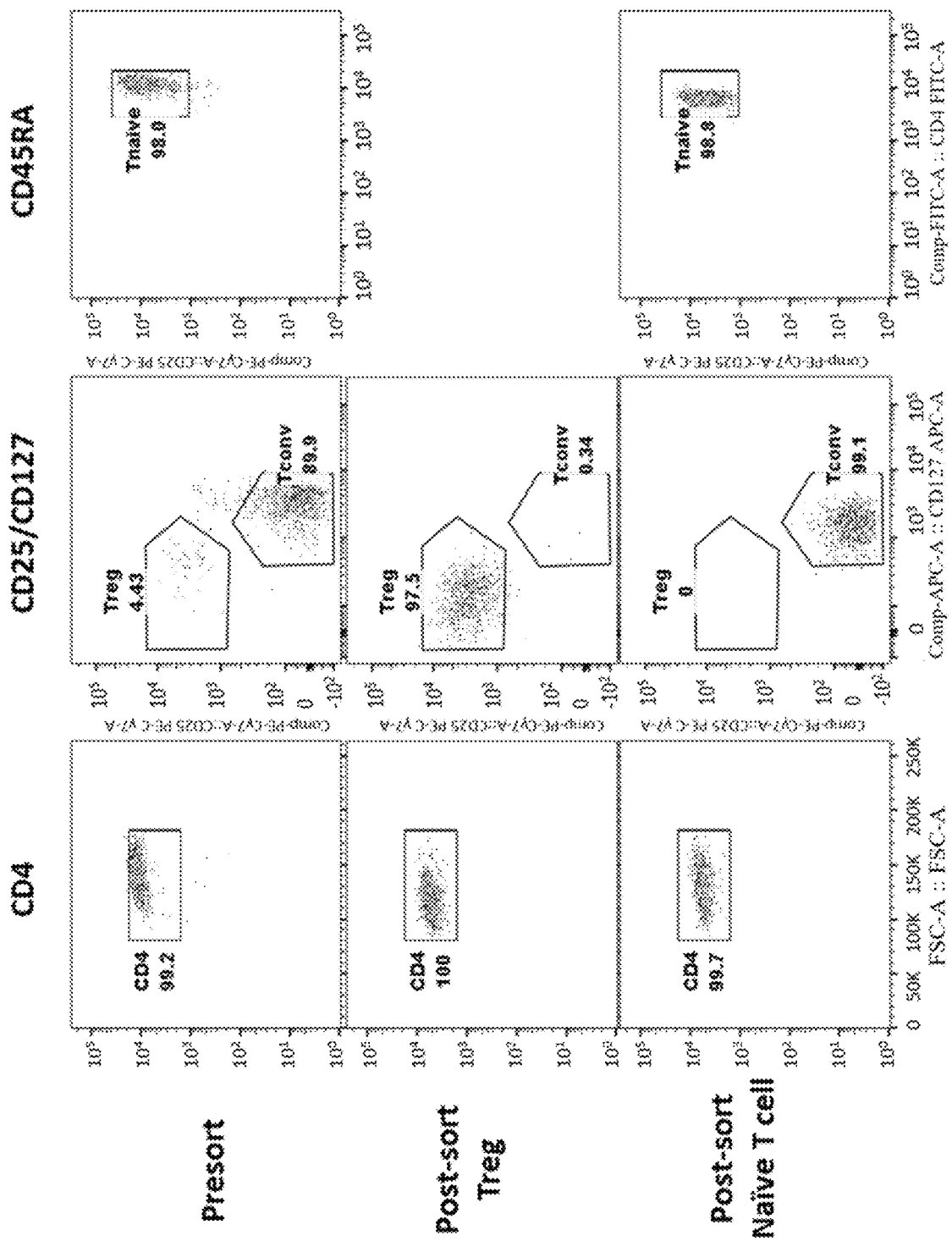
FIG. 2 shows a flow cytometry sorting strategy and purity.

First, CD4$^+$ T cells were isolated from human umbilical cord blood using CD4 microbeads (FIG. 2 top-panel, pre-sort) and sorted on FACSMelody™ sorter into Treg and naïve T cells according to the expression level of CD25, CD127, and CD45RA. To exclude non-CD4 expressing cells, a "lymphocyte gate" was performed followed by gating of the CD4$^+$ population. And then, naïve T cells and Treg populations were gated with CD25$^{hi}$CD127$^{lo}$ and CD25$^{low/-}$ CD127$^+$CD45RA$^+$, respectively as shown in FIG. 2. These gating strategies were applied to isolate Tregs from PBMCs. Both sort-isolated Treg and naïve T cell populations showed high purity above 97% (FIG. 2 post-sort Treg and naïve T cell). These sorted cells were cultured to expand over 2 weeks.

Phenotypic Analysis of nTreg and iTreg from UCB and PBMC

Figure 3:
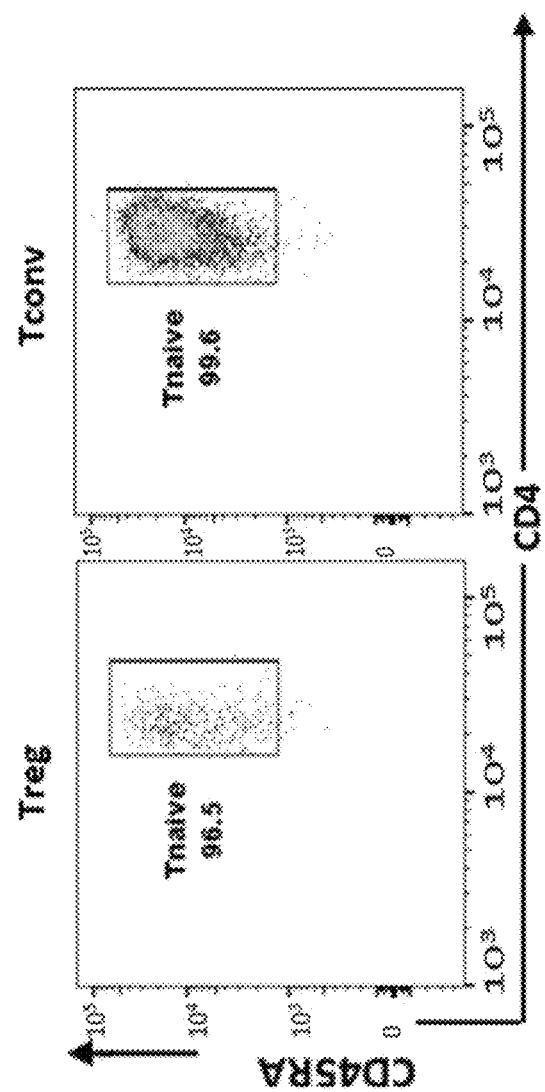
FIG. 3 shows identification of Treg and naïve T cell population in whole umbilical cord blood (UCB) and peripheral blood mononuclear cell (PBMC) on day 0.
Figure 3:
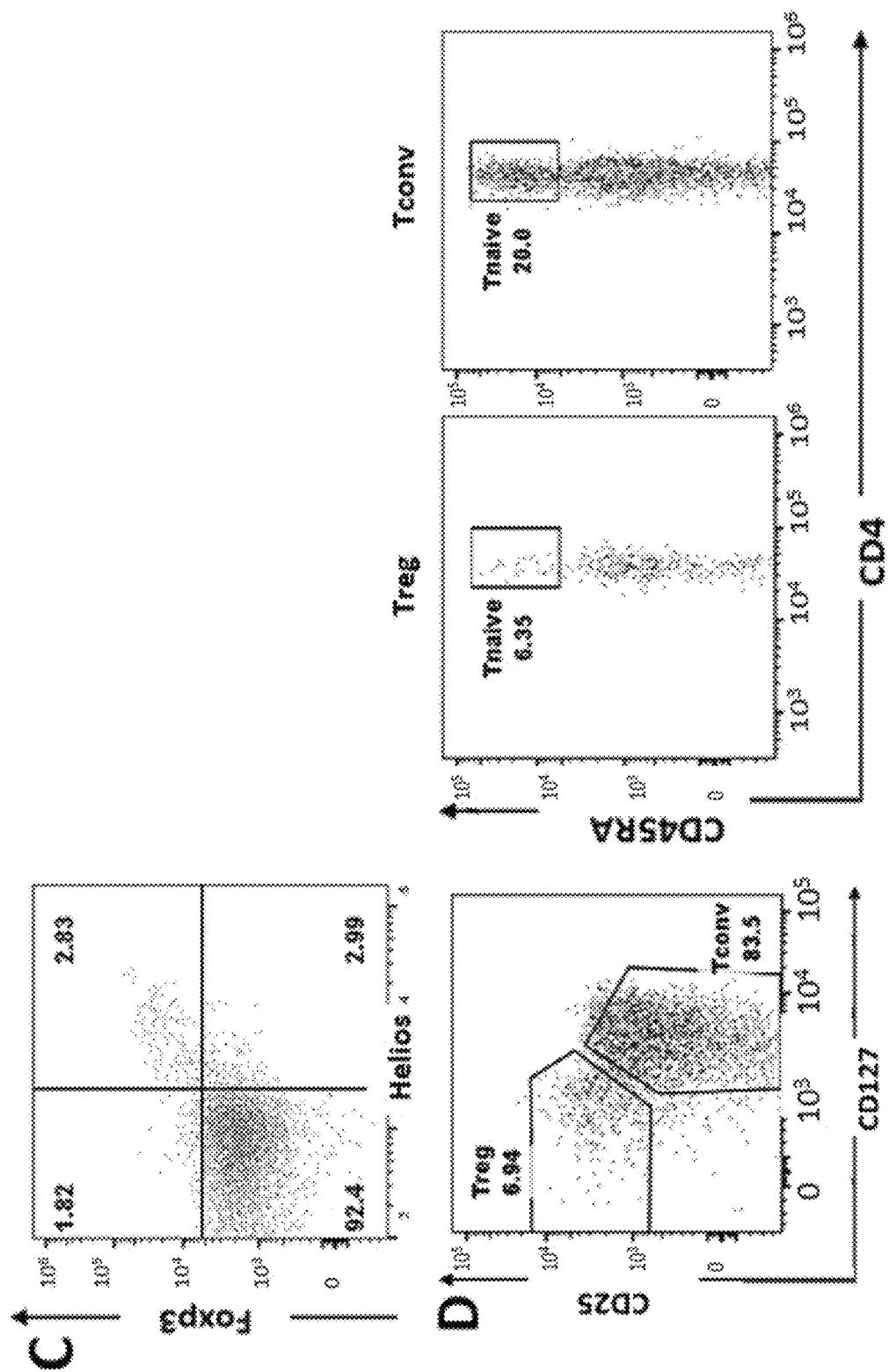

Both frozen umbilical cord blood (UCB) and peripheral blood mononuclear cell (PBMC) were thawed and subjected to analyze the phenotype before the enrichment of CD4$^+$ T cells on day 0 (FIG. 3). The Foxp3$^+$Helios$^+$ population shows CD25$^{hi}$CD127$^{lo}$ in UCB CD4$^+$ population. On the other hand, Foxp3$^-$Helios$^-$ population shows CD25$^{low/-}$ CD127$^+$CD45RA$^+$ (A of FIG. 3). To identify both Treg and naïve T cells in UCB, they were analyzed by CD25 and CD127 expression levels in the CD4$^+$ population as shown in B of FIG. 3. Then, they were gated by CD45RA expression level. From Treg and conventional T cells, both showed above 96% of CD45RA$^+$ naïve T cell populations showing a very high frequency of naïve T cells in UCB. It can be a unique characteristic of UCB derived cells distinguished by PBMC. Since UCB is never exposed to antigens from outside of a woman's body until the baby's birth, immune cells in UCB cannot have any chance to be matured. With the same gating strategy, cells derived from PBMC were analyzed as shown in C and D of FIG. 3. In contrast with UCB, both Treg and conventional T cells showed a lower percentage of CD45RA expression because immune cells in adult PBMC have met diverse antigens.

Figure 4:
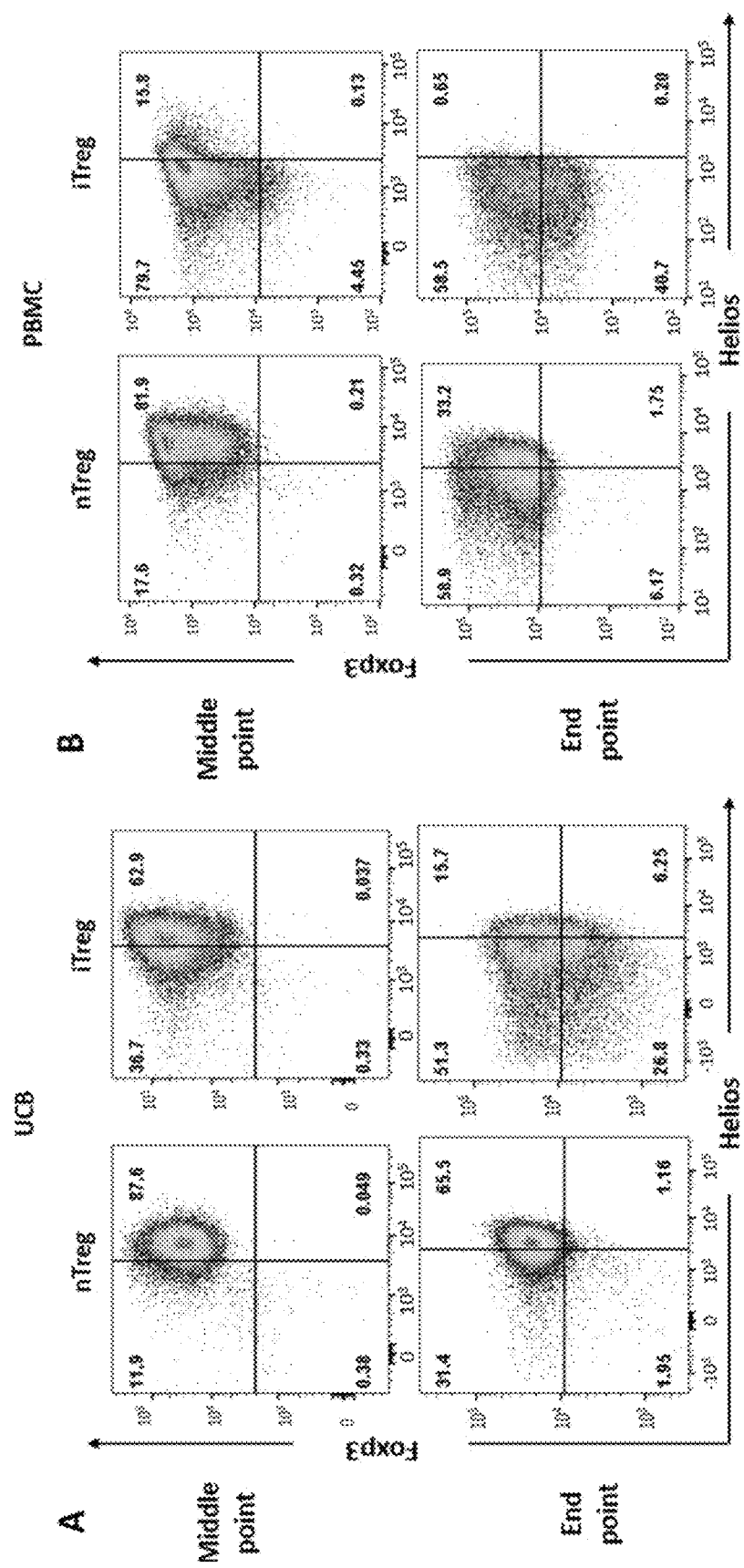
FIG. 4 shows a phenotypic analysis of expanded nTreg and iTreg in the middle and endpoint of the expansion. Cells were analyzed for Foxp3 and Helios intracellular staining as middle point analysis on days 10 to 12. In addition, the endpoint analysis was conducted on days 17 to 19. Both Foxp3 and Helios levels were shown in expanded nTreg and iTreg from UCB (A) and PBMC (B). All data were analyzed in a live $CD4^+$ population.

In a phenotypic analysis including Foxp3 and Helios expression level, the Foxp3+Helios+ population of nTregs derived from UCB was 87.6% at the middle point and it was decreased to 65.5% at the endpoint (A of FIG. 4). In the case of iTregs from UCB, Foxp3 and Helios double-positive populations were decreased from 62.9% to 15.7%. Even though both cells were cultured in the same condition, nTregs is better to maintain characteristics of Treg than iTregs over the culture periods. In B of FIG. 4, characteristics in both nTregs and iTregs derived from PBMC were analyzed by the same strategy. The nTreg at the middle point of culture showed approximately 92% of Foxp3+Helios+ populations similar to UCB but it declined to 33.2% at the endpoint. The Foxp3 and Helios double-positive populations in iTreg from PBMC were changed from 15.8% to below 1% during the expansion in vitro.

Cytokine Analysis of nTreg and iTreg Derived from UCB and PBMC

Figure 5:
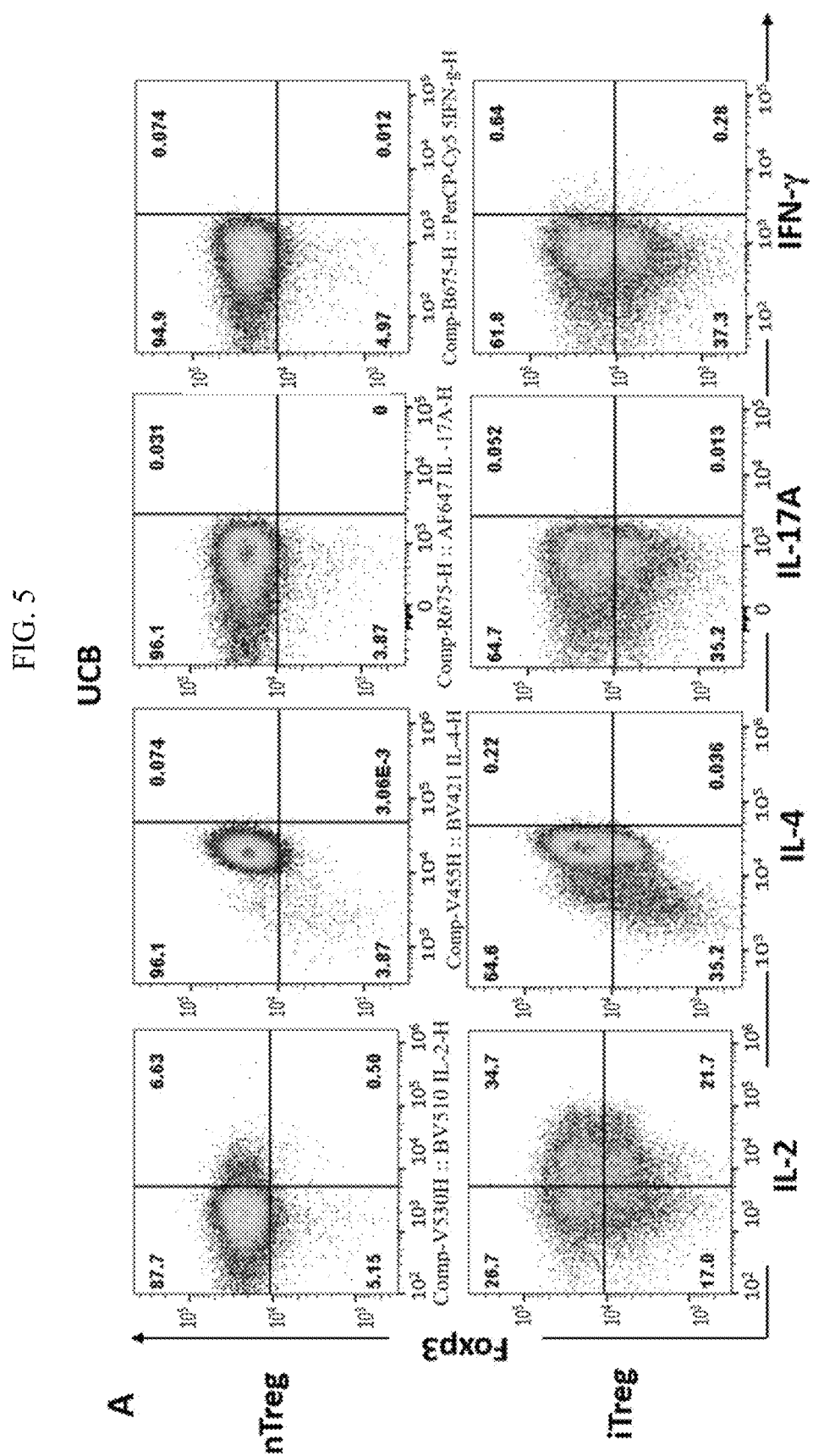
FIG. 5 shows a cytokine analysis of nTreg and iTreg derived from umbilical cord blood (UCB) and peripheral blood mononuclear cell (PBMC) at the endpoint of the expansion. Rested nTregs and iTregs were restimulated for 4 hours with PMA and ionomycin in the presence of brefeldin A. Intracellular IL-2, IL-4, IL-17A, and IFN-γ levels were analyzed from UCB (A) and PBMC (B) derived expanded nTregs and iTregs.
Figure 5:
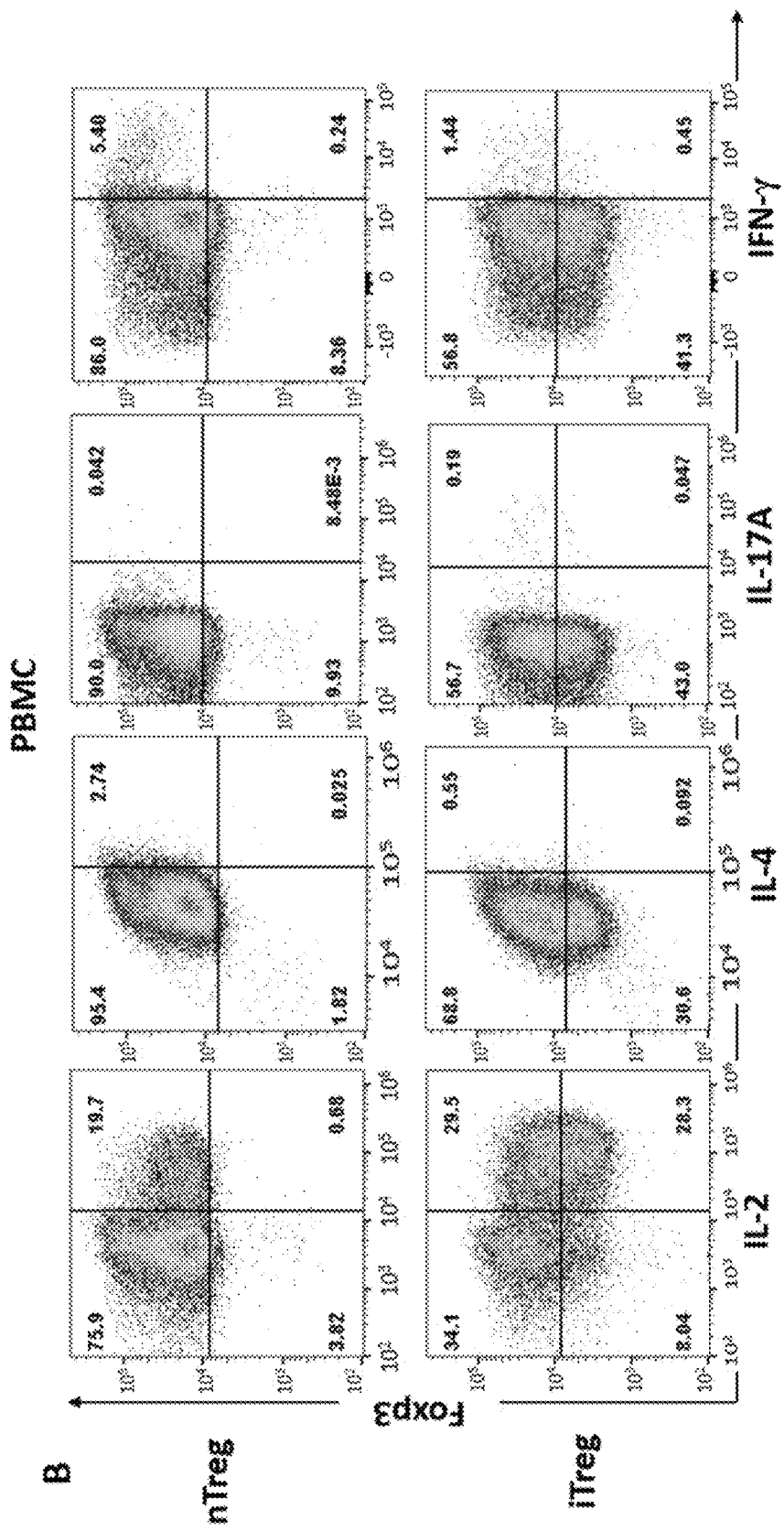

The cytokine production by both nTreg and iTreg derived from umbilical cord blood (UCB) or peripheral blood mononuclear cell (PBMC) was measured to address the plasticity of T cells in long-term expansion. The intracellular cytokine levels of IL-2, IL-4, IL-17A, and IFN-γ were measured by a flow cytometer. Both nTreg and iTreg from UCB and PBMC rarely secreted IL-4 and IL-17A. However, iTreg from UCB and PBMC secreted IL-2 (~35%, FIG. 5). The UCB derived nTreg secreted 6.63% of IL-2, but 19.7% of IL-2 was secreted in nTreg derived from PBMC. This result demonstrated that expanded nTreg did not differentiate into any lineages and retain their Treg stability during in vitro culture periods. In addition, it indicates that the Treg expansion technique (a method for producing a population of regulatory T cells by culturing an initial population of regulatory T cells obtained from umbilical cord blood in a media comprising an oligonucleotide of SEQ ID NO. 1 to expand the initial population of regulatory T cells) according to the present disclosure is reliable for maintaining phenotypic characteristics of Tregs including immunosuppressive function.

Figure 6:
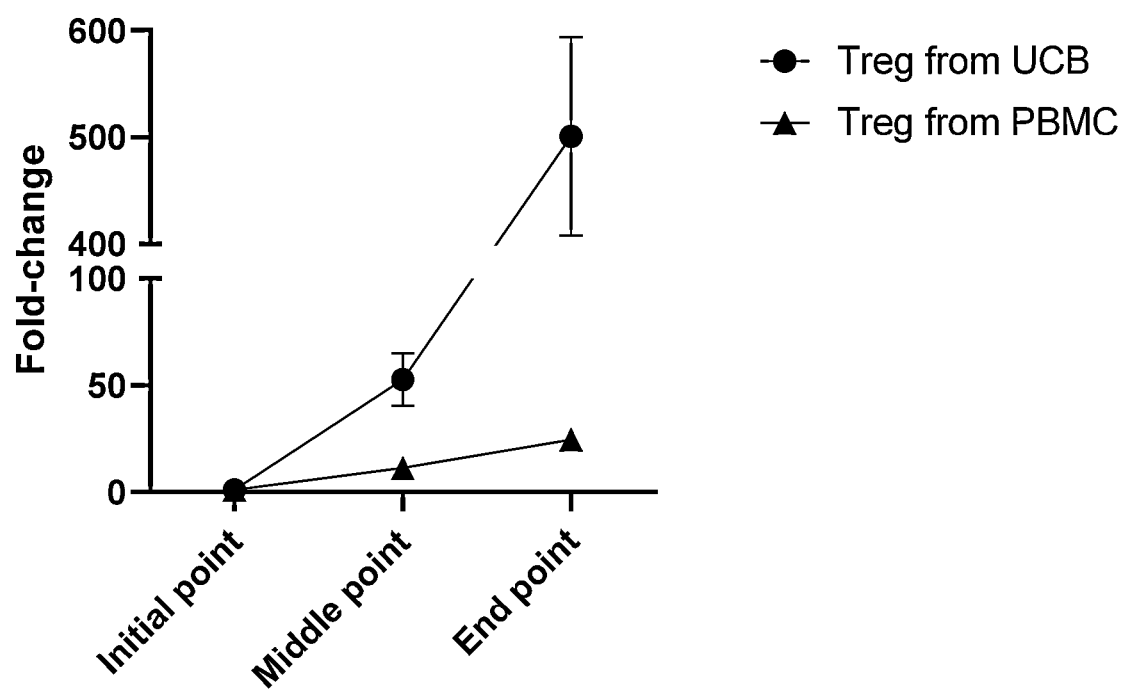
FIG. 6 shows a fold-change comparison between nTreg derived from umbilical cord blood (UCB) and peripheral blood mononuclear cell (PBMC) at the middle and endpoint of the expansion.

Fold-Change of nTreg Number from UCB and PBMC at the Middle and Endpoint of the Expansion In FIG. 6, it is shown that the number of expanded nTreg derived from PBMC were increased slightly from 11.3 times to 24.6 times. In contrast, the number of expanded UCB derived nTreg was dramatically increased from 52.6 times to 500.8 times at the endpoint of culture. Therefore, it was confirmed that the method according to the present disclosure (a method for producing a population of regulatory T cells by culturing an initial population of regulatory T cells obtained from umbilical cord blood in a media comprising an oligonucleotide of SEQ ID NO. 1 (or additionally comprising TGFβ1, and rapamycin) to expand the initial population of regulatory T cells) results in a high yield from UCB derived nTreg as compared to one from PBMC.

REFERENCES

1. Schmitt E G and Williams C B *Front. Immunol.* 2013; 4(152):1-13
2. Sharvan Sehrawat, Barry T. Rouse *J Leukoc Biol.* 2011; 90(6): 1079-1087
3. Roncarolo M G, Battaglia M., *Nat Rev* Immuno., 2007; 7(8):585-598
4. Riley J L, June C H, Blazar B R, Immunity, 2009; 30(5):656-665
5. Hoffmann P, Ermann J, Edinger M, Fathman C G, Strober S, *J Exp Med,* 2002; 196(3):389-399
6. Liu W, Putnam A L, Xu-Yu Z, et al., *J Exp Med.* 2006; 203(7):1701-1711
7. Hippen K L, Merkel S C, Schirm D K, et al., *American Journal of Transplantation,* 2011; 11(6): 1148-1157
8. Hoffmann, P, Eder, R, Boeld, T J, Doser, K, Piseshka, B, Andreesen, R, et al. *Blood* 2006; 108: 4260-4267

What is claimed is:

1. A method for producing a population of regulatory T cells comprising:
    culturing an initial population of regulatory T cells obtained from umbilical cord blood in a media comprising an oligonucleotide of SEQ ID NO. 1 to expand the initial population of regulatory T cells.

2. The method of claim 1, wherein the media further comprises TGFβ1.

3. The method of claim 1, wherein the media further comprises rapamycin.

4. The method of claim 1, wherein the media further comprises TGFβ1 and rapamycin.

5. The method of claim 1, wherein the initial population of regulatory T cells has been enriched for CD4+ CD25+/hiCD127lo/− FoxP3+.

* * * * *

SEQUENCE LISTING

<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: BHKps25

<400> SEQUENCE: 1
aatcgtaacc gtcgtatcgg cgat                                          24